United States Patent [19]

Schiweck et al.

[11] Patent Number: 4,816,078

[45] Date of Patent: Mar. 28, 1989

[54] PROCESS FOR PRODUCTION OF CRYSTALLINE L-ARABINOSE

[75] Inventors: Hubert Schiweck, Worms; Manfred Vogel, Grünstadt, both of Fed. Rep. of Germany

[73] Assignee: Suddeutsche Zucker-Aktiengesellschaft, Mannheim, Fed. Rep. of Germany

[21] Appl. No.: 146,669

[22] Filed: Jan. 21, 1988

[30] Foreign Application Priority Data

Dec. 22, 1987 [DE] Fed. Rep. of Germany ....... 3702653

[51] Int. Cl.$^4$ ............................................. C13K 13/00
[52] U.S. Cl. ........................................ 127/36; 127/37; 127/44; 127/43; 127/53; 127/55; 127/58; 127/46.2; 127/46.1
[58] Field of Search ..................... 127/37, 36, 43, 44, 127/53, 55, 58, 46.2, 46.1, 46.3

[56] References Cited

U.S. PATENT DOCUMENTS

| 4,516,566 | 5/1985 | Chao et al. | 127/37 |
| 4,591,388 | 5/1986 | Chao et al. | 127/37 |

FOREIGN PATENT DOCUMENTS

| 129664 | 4/1968 | Czechoslovakia . | |
| 137537 | 12/1969 | Czechoslovakia . | |
| 0115068 | 8/1984 | European Pat. Off. . | |
| 143261 | 8/1980 | Fed. Rep. of Germany . | |

OTHER PUBLICATIONS

A. E. Goodban and H. S. Owens (J. Am. Soc. Sugar Beet Technol. 9, 129–132, 1956).
S. Harding (Sugar 24, 656, 1922).
L. Sands (Org. Synth. 1, 67, 1941).

*Primary Examiner*—Curtis R. Davis
*Assistant Examiner*—Chung K. Pak
*Attorney, Agent, or Firm*—Armstrong, Nikaido, Marmelstein & Kubovcik

[57] ABSTRACT

The invention concerns a process for production of L-arabinose in crystalline form. Starting material are extracted sugar beet pulp or other L-araban containing plant materials. These are heated in an autoclave as an aqueous suspension in the presence of $Ca(OH)_2$. The so obtained solution is chromatographed on a cationic exchanger in the Ca-form. The araban containing fraction is hydrolyzed after adding $H_2SO_4$, neutralized and rechromatographed on a cationic exchanger in Ca-form. After concentrating the arabinose containing fractions L-arabinose is obtained in form of crystals by cooling crystallization.

6 Claims, 2 Drawing Sheets

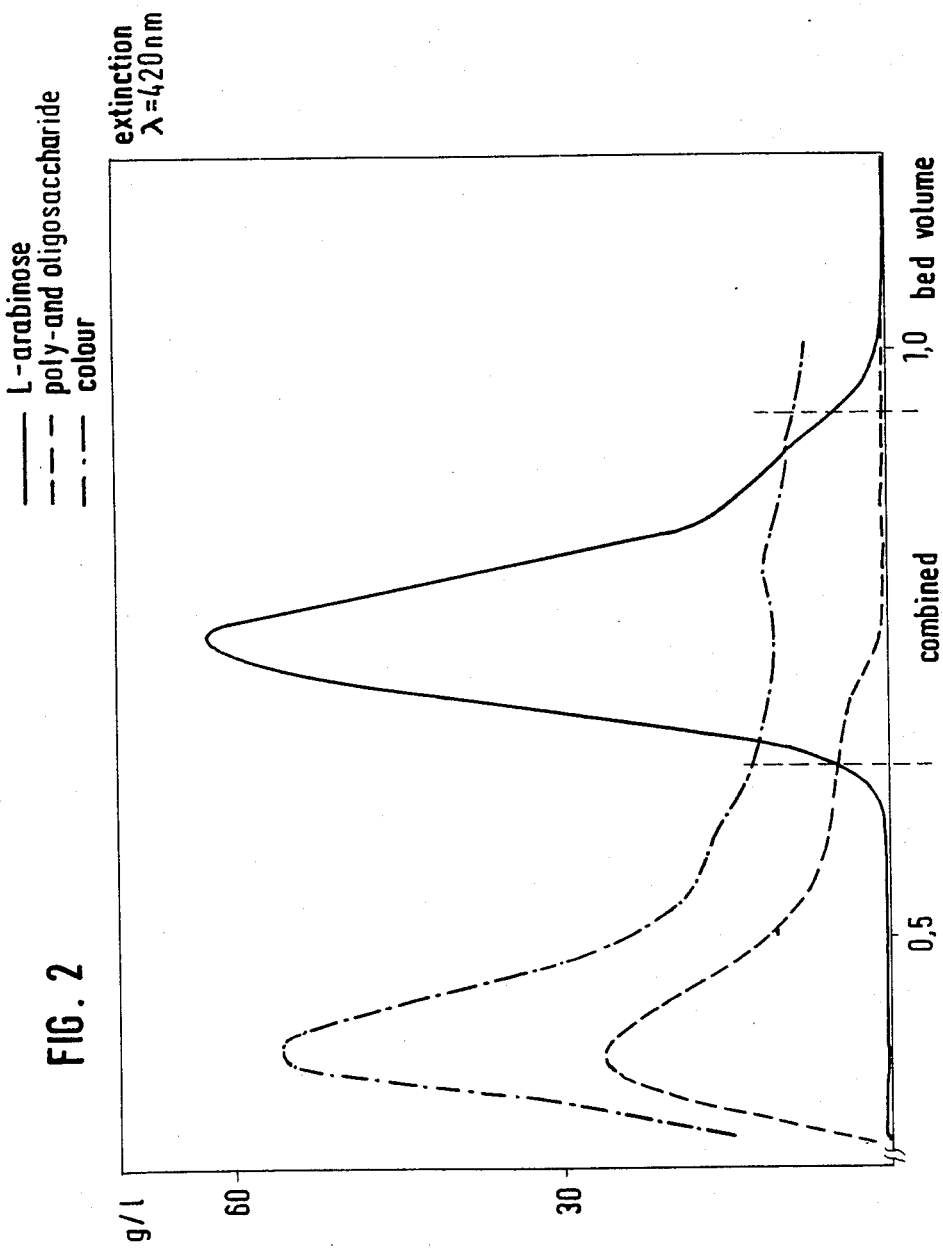

PROCESS FOR PRODUCTION OF CRYSTALLINE L-ARABINOSE

The invention concerns a process for production of L-arabinose from araban containing plant material, especially beet araban, which was isolated from beet pulp after sugar extraction. Araban occurs in many plant gums like gum arabicum, cherry gum, but also as a component of beet marc. In nature araban is always associated with pectin. The araban molecule has a relative low molecular weight and is not only built up of a linear α-1,5 linked arabinofuranoside chains but shows also α-1,3-linkages, therefore araban seems to be a highly branched polysaccharide. Araban is not a homopolymer, which contains only the monosaccharide L-arabinose. After acid hydrolysis of beet araban D-galactose, L-rhamnose and D-galacturonic acid can be detected as main components beside after monosaccharides.

One way, to isolate L-arabinose from plant material, exists in acid hydrolysis of the starting material, followed by the isolation of L-arabinose out of the solution. Such trials have been described by S. Harding (Sugar 24, 656, 1922). E. Anderson and L. Sands (Org. Synth. 1, 67, 1941) describe the isolation of L-arabinose taking mesquite-gum as starting material. The product solution obtains beside L-arabinose also high amounts of other carbohydrates. Therefore complicated isolation steps are necessary. Patents CS 129 664 and 137 537 describe a process to remove such carbohydrates. This is done by fermentation with yeast after neutralisation of the acid hydrolysate, followed by precipitation of the high molecular weight contaminations with ethanol. Finally L-arabinose will be crystallized from the ethanolic solution. Beside the acid hydrolyses the extraction of araban in alkali medium is described by A. E. Goodban and H. S. Owens (J. Am. Soc. Sugar Beet Technol. 9, 129–132, 1956). They showed that araban is extracted at 100° C., pH 11 and 40 minutes in nearly quantitative amounts. In presence of enough lime milk and identical temperature similar results can be obtained after a two hour incubation time.

In the patent DD-PS No. 143 261 beet pulp is washed extensively with water, to remove the remaining sucrose; followed by extraction of araban with a Ca(OH)$_2$ solution at a temperature of 80° to 100° C., preferably 95° C. and a residence time of 10 to 120 minutes, preferable 30 minutes.

EP-A-No. 0115 068 describes the separation of L-arabinose by selective adsorption on zeolites. Binding of other carbohydrates shall not occur. L-arabinose is eluted with water or watery mixtures of alcohols or ketones. Surprisingly it was found that L-arabinose can be obtained in cristallized form with good yield from pure watery solutions, when araban is extracted from beet pulp at elevated temperature and pressure in an alkaline medium. Under these circumstances araban is fast and nearly quantitatively extracted. In contrast to other procedures a pretreatment of the plant material like extensive washing is not necessary. The concentrations of Ca(OH)$_2$ in this solution are 0.5 to 2.0% (w/w) respectively a ratio of 6 to 17% (w/w) per kg dry substance. The residence time is 2 to 20 minutes at a temperature of 105° to 160° C., corresponding a pressure of 1.5 to 7 bar. Under these conditions the major part of the pectin is destroyed. In this case the pressure is higher than the pressure of saturated steam. After cooling on 40° to 60° C. for example the alkaline reaction solution is neutralised under mixing by addition of acid especially sulfuric acid. The undissolved plant residues and the inorganic precipitate are separated from the araban containing solution by filtration. The so obtained araban containing solution is concentrated to 40 to 60% dry substance by evaporation and if necessary again filtered. Furthermore, the invention concerns the isolation of L-arabinose by chromatography. First, the araban containing solution is fractionated on a cationic-exchanger in Ca-form. This is done best at 70° to 80° C. Separation is done under similar conditions as described for the separation of glucose and fructose starting with invert sugar.

BRIEF DESCRIPTION OF THE DRAWING

FIGS. 1 and 2 are graphs dealing with carbohydrate concentrations v. combined bed volume.

As shown in FIG. 1 araban is eluted first, followed by sucrose and ionic substances. Sucrose comes from the extracted beet pulp, and ionic substances are Ca-salts of organic acids, which are degradation products of pectin. The araban containing fractions, approximately 0.5 bed volume, are hydrolysed after addition of H$_2$SO$_4$; therefore the solution is brought to 0.5 to 2% (w/w), especially 1% (w/w) with acid. The hydrolysis process is done at a temperature of 92° to 97° C. and a reaction time of 50 to 80 minutes, especially at 93° to 95° C. and 70 minutes. Under these conditions L-arabinose is extracted from araban nearly completely and other carbohydrates like D-galactose, L-rhamnose and D-galacturonic acid remain in oligomeric/polymeric form. The neutralisation of this hydrolysed solution is done by adding CaCO$_3$. The obtained precipitate is separated by filtration and concentrated by evaporation to 40 to 60% dry substance followed by filtration and separation on a cationic exchanger in Ca-form is done with water at raised temperatures, for example 70° to 80° C. FIG. 2 shows, that existing coloured impurities and polymeric carbohydrates are eluted first followed by L-arabinose, which shows a purity of 85 to 89%. According to the invention the L-arabinose containing fractions possess such a high purity, that L-arabinose can be crystallized from water as described in the next step.

Figure 1:
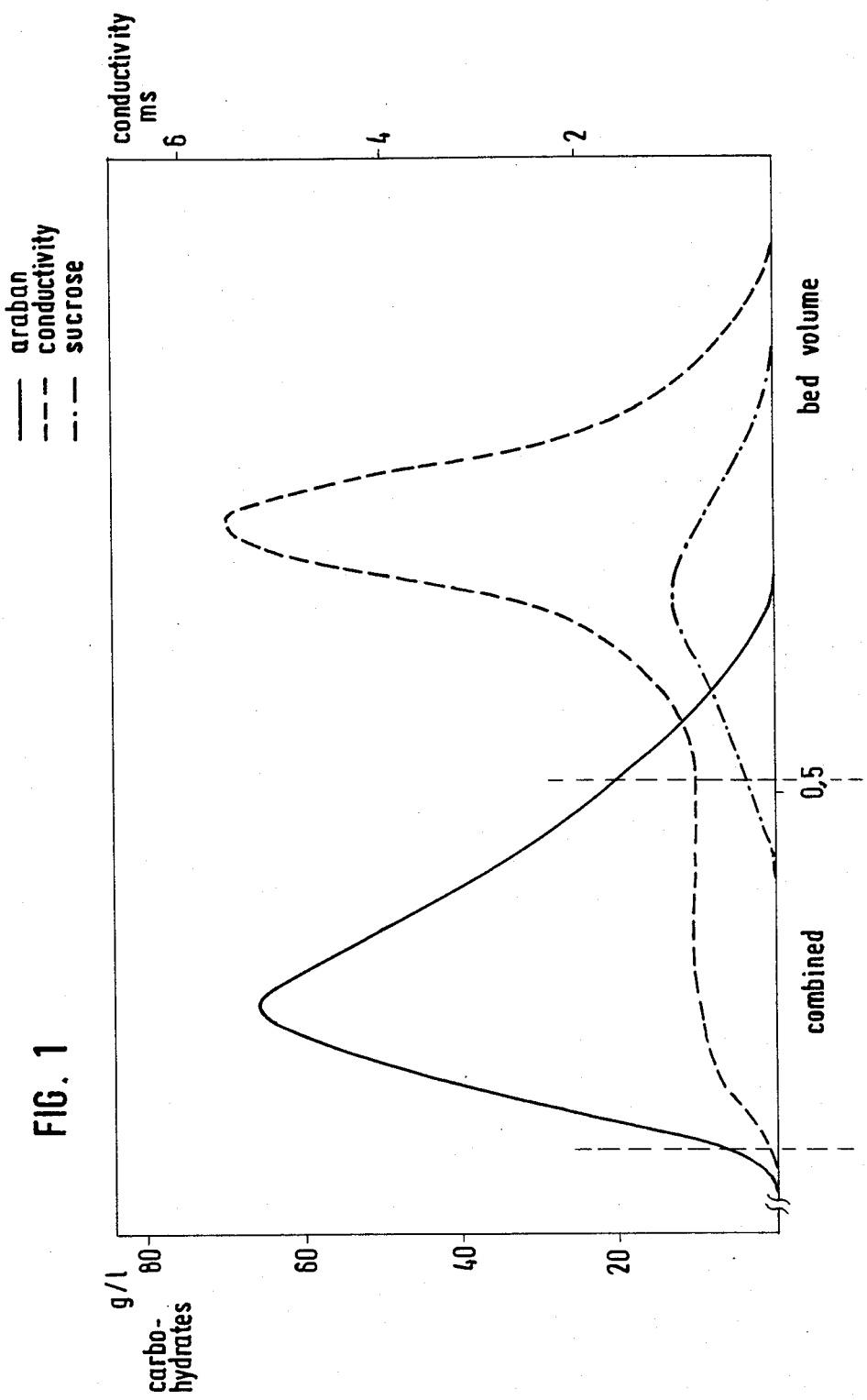

The combined L-arabinose containing fractions are concentrated to 60 to 80% dry substance, especially 65%, followed by a cooling crystallization, where for example the solution is cooled down from 65° to 25° C. L-arabinose with a purity of 94 to 97% is obtained by this procedure. A recrystallization in water gives a purity >98%. Normally, the crystallization is done in multiple steps. In this case for example the syrup after the third crystallization is brought back to the second chromatography step on the cationic-exchanger in the Ca-form. As cationic-exchanger, a material is taken whose matrix consists of polystyrene acid in Ca-form, cross-linked with 3 to 6% divinyl benzene, e.g. Lewatit TSW 40 of Bayer or Duolite C'204 F of Rohm & Haas. The following are examples of the process of the present invention:

EXAMPLE 1

150 kg beet pulp (27% dry substance) is heated quickly (10 minutes) up to 140° C. with 300 l water in the presence of 5.3 kg Ca(OH)$_2$ under mixing. Reaction time is 5 minutes. The cooled slurry is neutralized with H$_2$SO$_4$ (33%). After separation of the remaining solids and washing of the same with 100 liter water, the solutions are combined and concentrated from 5 to 45% dry substance. After filtration the syrup is chromatographed with water at 80° C. on a 500 l separation unit with a weakly crosslinked cationic exchanger in the Ca-form (e.g. of the type TSW 40, Feinkorn (fine grain), of Bayer AG). The elution is done with 115 liter per hour. The araban containing fractions are combined and brought to 1% (w/w) $H_2SO_4$ with approximately 12 kg $H_2SO_4$ (33%). The hydrolysis is done at 93° C. for 70 minutes. The neutralisation is done by addition of approximately 5 kg $CaCO_3$, followed by filtration. The concentrated (45% dry substance) and filtered solution is again chromatographed on a 330 liter separation unit, filled with the same cationic exchanger in Ca-form. Chromatography is done at same conditions. The L-arabinose containing fractions are combined and concentrated to 65% dry substance at 65° C. followed by a multi step cooling crystallization. Cooling is taking place with 3° C. per hour. The obtained crystals are separated by filtration. There is a yield of 2.7 kg with 95% purity.

EXAMPLE 2

In a autoclave 4.6 kg dried beet pulp (93% dry substance) is mixed with 35 liters hot water (95° C.), which contains 600 g $Ca(OH)_2$. Heating up to 140° C. under mixing is done quickly; the slurry remains at this temperature for 5 minutes. For further steps see example 1. The yield of L-arabinose is 260 g.

EXAMPLE 3

200 kg beet pulp (27% dry substance) is heated up to 140° C. in a second by simultaneous addition of 120 liters of an aqueous $Ca(OH)_2$ suspension, which contains 6 kg $Ca(OH)_2$ in total. Reaction time at this temperature is 4 minutes. The cooled slurry is neutralized by addition of $H_2SO_4$ (33%) and the araban containing liquid is separated with a membrane filter press. Water in twice the volume of the filter cake is taken for washing. For further steps see example 1. The yield of L-arabinose is 3.9 kg.

We claim:

1. Process for production of crystalline L-arabinose from an araban containing plant material by disintegration in a $Ca(OH)_2$ containing suspension, characterized by
   (a) dissolving the araban at temperatures between 105° C. and 160° C. at an adjusting pressure obtained in a closed vessel for a reaction period of 2 to 20 minutes by the use of an aqueous reaction solution so that a final concentration of 0.5 to 2% by weight of $Ca(OH)_2$ is existing corresponding to a ratio of 6 to 17% by weight $Ca(OH)_2$ per kg of said plant material,
   (b) neutralizing the resulting reaction solution with an acid after cooling and followed by a filtration step to separate the resulting undissolved plant material and the resulting inorganic precipitate,
   (c) concentrating the obtained aqueous phase to 40 to 60% by weight of said araban by evaporation and followed by a separation step taking a strong acid, weakly cross-linked cationic exchanger in Ca-form to get an araban containing fraction and a by-product fraction,
   (d) hydrolyzing the araban containing fraction with a 0.5 to 2% by weight aqueous $H_2SO_4$ solution at a temperature of 92° C. to 97° C. for 50 to 80 minutes,
   (e) neutralizing the hydrolyzed solution of step (d) by adding $CaCO_3$, separating the formed precipitate by filtration and concentrating the resulting precipitate removed solution to 40 to 60% by evaporation,
   (f) separating the concentrated solution of step (e) by a strong acid, weakly cross-linked cationic exchanger in Ca-form into an L-arabinose containing fraction and a by-product fraction,
   (g) subjecting the arabinose containing fraction after concentration to 60 to 80%, to cooling crystallization and separating the resulting crystals.

2. Process according to claim 1, characterized in that the disintegration of the araban containing material is done in a temperature range of 130° C. to 140° C. at a mean residence time of 5 to 10 minutes.

3. Process according to claims 1 or 2, characterized in that the reaction solution contains 1 to 1.5% by weight $Ca(OH)_2$.

4. Process according to claim 1, characterized in that the araban containing fraction is hydrolyzed in a 0.8 to 1.2% by weight aqueous $H_2SO_4$ solution at 93° C. to 95° C. for 70 minutes.

5. Process according to claim 2, characterized in that the araban containing fraction is hydrolyzed in a 0.8 to 1.2% by weight aqueous $H_2SO_4$ solution at 93° C. to 95° C. for 70 minutes.

6. Process according to claim 3, characterized in that the araban containing fraction is hydrolyzed in a 0.8 to 1.2% by weight aqueous $H_2SO_4$ solution at 93° C. to 95° C. for 70 minutes.

* * * * *

UNITED STATES PATENT AND TRADEMARK OFFICE
CERTIFICATE OF CORRECTION

PATENT NO. : 4,816,078

DATED : March 28, 1989

INVENTOR(S) : SCHIWECK et al

It is certified that error appears in the above-identified patent and that said Letters Patent is hereby corrected as shown below:

On the cover page, Item [30], line 2, "Dec. 22, 1987" should read --Jan. 29, 1987--.

Signed and Sealed this

Seventh Day of May, 1991

*Attest:*

HARRY F. MANBECK, JR.

*Attesting Officer*     *Commissioner of Patents and Trademarks*